US00PP16376P2

(12) United States Plant Patent
Jepsen

(10) Patent No.: US PP16,376 P2
(45) Date of Patent: Mar. 21, 2006

(54) ***KALANCHOE* PLANT NAMED 'KJ 2001 0934'**

(50) Latin Name: *Kalanchoe blossfeldiana*
Varietal Denomination: KJ 2001 0934

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 10/917,148

(22) Filed: Aug. 12, 2004

(51) Int. Cl.
*A01H 5/00* (2006.01)

(52) U.S. Cl. ..... Plt./335

(58) Field of Classification Search ..... Plt./335, Plt./339
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Kalanchoe* plant named 'KJ 2001 0934', characterized by its upright and compact plant growth habit; small, dark green-colored leaves; light red purple-colored flowers; and excellent postproduction longevity.

1 Drawing Sheet

Botanical classification/cultivar designation: *Kalanchoe blossfeldiana* cultivar KJ 2001 0934.

BACKGROUND OF THE INVENTION

The present invention relates to a new and distinct cultivar of *Kalanchoe* plant, botanically known as *Kalanchoe blossfeldiana,* and hereinafter referred to by the name 'KJ 2001 0934'.

The new *Kalanchoe* is a product of a planned breeding program conducted by the Inventor in Hinnerup, Denmark. The objective of the breeding program was to create new freely-flowering *Kalanchoe* cultivars with large flowers, small leaves and excellent postproduction longevity.

The new *Kalanchoe* originated from a cross-pollination made in Hinnerup, Denmark of the *Kalanchoe blossfeldiana* cultivar Simone 2000, disclosed in U.S. Plant Pat. No. 12,319, as the female, or seed, parent with the *Kalanchoe* cultivar Anatole, not patented, as the male, or pollen, parent. The new *Kalanchoe* was discovered and selected by the Inventor as a single flowering plant within the progeny of the stated cross-pollination grown in a controlled environment in Hinnerup, Denmark.

Asexual reproduction of the new *Kalanchoe* by terminal cuttings at Hinnerup, Denmark, by the Inventor, has shown that the unique features of this new *Kalanchoe* are stable and reproduced true to type in successive generations.

BRIEF SUMMARY OF THE INVENTION

The cultivar KJ 2001 0934 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'KJ 2001 0934'. These characteristics in combination distinguish 'KJ 2001 0934' as a new and distinct cultivar of *Kalanchoe:*

1. Upright and compact plant growth habit.
2. Small, dark green-colored leaves.

3. Light red purple-colored flowers.
4. Excellent postproduction longevity.

Plants of the new *Kalanchoe* are most similar to plants of the parent cultivars and differ primarily from plants of the parent cultivars in leaf size, flower size and flower color.

Plants of the new *Kalanchoe* can be compared to plants of the cultivar Helene, disclosed in U.S. Plant Pat. No. 14,963. In side-by-side comparisons conducted in Hinnerup, Denmark, plants of the new *Kalanchoe* differed from plants of the cultivar Helene in the following characteristics:

1. Plants of the new *Kalanchoe* were stronger than plants of the cultivar Helene.
2. Plants of the new *Kalanchoe* had smaller leaves than plants of the cultivar Helene.

BRIEF DESCRIPTION OF THE PHOTOGRAPHS

The accompanying colored photographs illustrate the overall appearance of the new *Kalanchoe,* showing the colors are true as it is reasonably possible to obtain in colored reproductions of this type. Colors in the photographs may differ slightly from the color values cited in the detailed botanical description which accurately describe the colors of the new *Kalanchoe.* The photographs were taken under diffuse natural light conditions on an overcast day at approximately noon in Hinnerup, Denmark.

The photograph at the top of the sheet comprises a side perspective view of a typical potted plant of 'KJ 2001 0934'.

The photograph at the bottom of the sheet comprises a top perspective view of a typical plant of 'KJ 2001 0934'.

DETAILED BOTANICAL DESCRIPTION

In the following description, color references are made to The Royal Horticultural Society Colour Chart, 1995 Edition, except where general terms of ordinary dictionary significance are used. Plants used in the photographs and for the following observations and measurements were grown in Hinnerup, Denmark, under commercial practice in a glass-covered greenhouse for about eleven weeks after the start of short day/long night photoperiodic treatment with average temperatures of 20° C. Plants used in the description and photographs were not pinched. Unless otherwise specified, the leaf description represents leaves from a vegetative plant.

Botanical classification: *Kalanchoe blossfeldiana* cultivar KJ 2001 0934.

Parentage:

*Female, or seed, parent.*—*Kalanchoe blossfeldiana* cultivar Simone 2000, disclosed in U.S. Plant Pat. No. 12,319.

*Male, or pollen, parent.*—*Kalanchoe blossfeldiana* cultivar Anatole, not patented.

Propagation:

*Type cutting.*—Terminal cuttings.

*Time to produce a rooted young plant.*—About two weeks.

*Root description.*—Numerous, fine, fibrous, and well-branched.

Plant description:

*Form.*—Upright plant habit with numerous compound cymes; freely flowering. Actual plant shape will depend on whether or not plants are pinched (apical terminals removed).

*Branching habit.*—Freely branching. Pinching (removal of terminal apex) is not required but will enhance lateral branch development.

*Plant height at flowering.*—About 16 cm.

*Plant diameter at flowering.*—About 22 cm.

*Foliage description.*—Arrangement: Opposite, simple. Size: Leaf size is reduced after floral induction. Vegetative plants: Length: About 10 cm. Width: About 6 cm. Reproductive plants: Length: About 5.5 cm. Width: About 5.5 cm. Shape: Ovate. Apex: Rounded. Base: Obtuse. Margin: Crenate; undulate. Aspect: Slightly concave. Texture, upper and lower surfaces: Glabrous; leathery; succulent. Color: Developing foliage, upper surface: 137A. Developing foliage, lower surface: 137C. Fully expanded foliage, upper surface: 147A. Fully expanded foliage, lower surface: 147B.

Flower description:

*Flower type and habit.*—Single flowers arranged in compound dichasial cymes that arise from leaf axils. Upright flowering stems. Freely flowering. Flowers persistent.

*Natural flowering season.*—Winter to early spring; flower initiation and development can be induced under short day/long night conditions.

*Time to flower.*—In the summer with 20° C. growing temperatures, about eleven weeks of short day/long night conditions are required to produce flowering plants. During the winter with supplemental lighting and 20° C. growing temperatures, about eleven weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, 50% of the remaining flowers are open.

*Post-production longevity.*—Plants of the new *Kalanchoe* maintain good leaf and flower substance for at least five weeks under interior environmental conditions.

*Inflorescence height.*—About 12 cm.

*Inflorescence diameter.*—About 6 cm.

*Flower diameter.*—About 1.9 cm.

*Quantity.*—Freely flowering; primary cymes with about 100 to 200 flowers each.

*Flower buds.*—Shape: Narrowly oblong. Length: About 1 cm. Width: About 4 mm. Color: 29B.

*Petals.*—Quantity per flower: Four fused at base. Length: About 9 mm. Diameter: About 7 mm. Shape: Round obovate. Apex: Cuspidate. Margin: Entire. Texture, upper and lower surfaces: Glabrous, smooth; satiny. Color: Upper surface: 69A; towards the base, 63B. Lower surface: 49D.

*Sepals.*—Calyx length: About 1 cm. Calyx diameter: About 3 mm. Texture, upper and lower surfaces: Smooth, glabrous. Color, upper and lower surfaces: 139D.

*Peduncles.*—Length: About 1.3 to 1.5 cm. Strength: Strong. Aspect: Mostly upright. Texture: Smooth, glabrous. Color: 144A.

*Pedicels.*—Length: About 3 to 5 mm. Strength: Strong. Aspect: Mostly upright. Texture: Smooth, glabrous. Color: 144A.

*Reproductive organs.*—Stamens: Stamen number: About six. Anther shape: Slightly oblong. Anther color: 14B. Filament color: Green, close to 145A. Pollen color: Yellow, close to 9A. Pistils: Pistil number: About four. Pistil length: About 8 mm. Style color: Light green, close to 145A. Stigma shape: Round. Ovaries: Superior and four-celled. Ovary size: About 6 mm by 1 mm. Ovary color: Light green, close to 145A.

*Seed/fruit.*—Seed and fruit production has not been observed.

Disease/pest resistance: Resistance to known pathogens and pests common to *Kalanchoe* has not been observed on plants of the new *Kalanchoe* grown under commercial greenhouse conditions.

It is claimed:

1. A new and distinct cultivar of *Kalanchoe* plant named 'KJ 2001 0934', as illustrated and described.

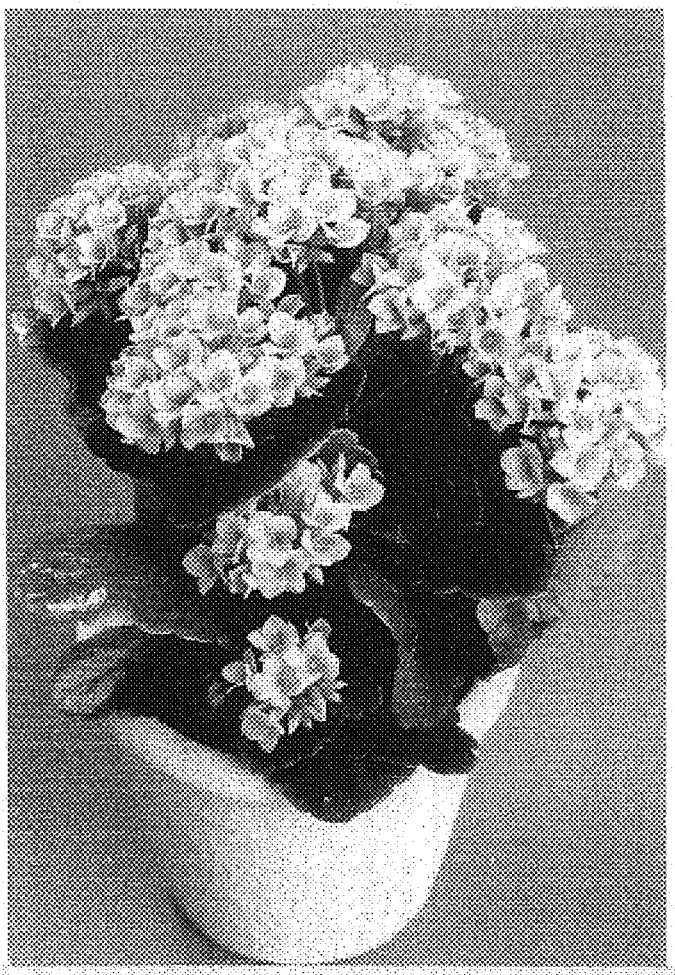
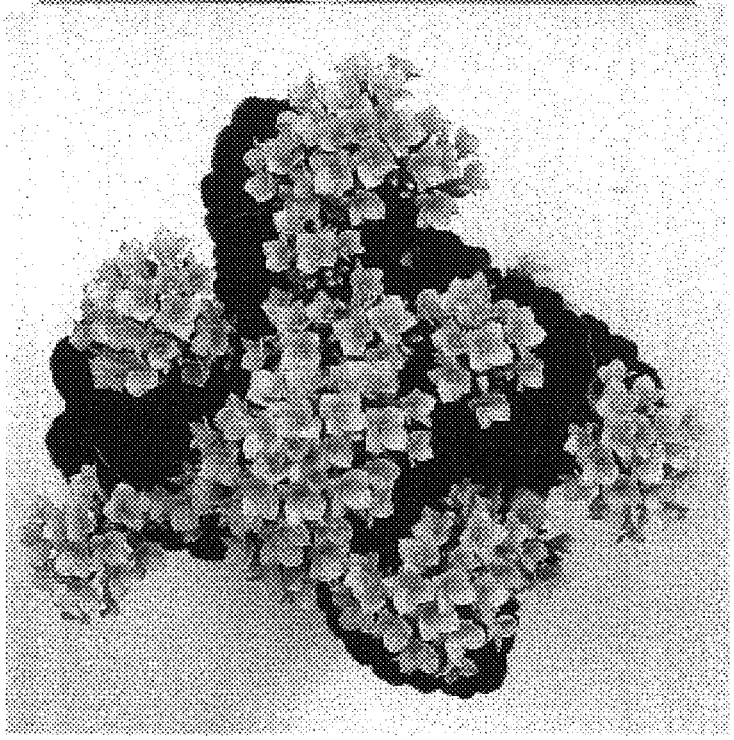

* * * * *